US010220162B2

(12) United States Patent
Vardi

(10) Patent No.: US 10,220,162 B2
(45) Date of Patent: Mar. 5, 2019

(54) PERICARDIAL ACCESS DEVICE AND ITS METHODS OF USE

(71) Applicant: Gil Vardi, St. Louis, MO (US)

(72) Inventor: Gil Vardi, St. Louis, MO (US)

( * ) Notice: Subject to any disclaimer, the term of this patent is extended or adjusted under 35 U.S.C. 154(b) by 1005 days.

(21) Appl. No.: 14/149,332

(22) Filed: Jan. 7, 2014

(65) Prior Publication Data
US 2015/0190611 A1  Jul. 9, 2015

(51) Int. Cl.
| | | |
|---|---|---|
| *A61M 5/50* | (2006.01) | |
| *A61M 5/158* | (2006.01) | |
| *A61M 25/01* | (2006.01) | |
| *A61M 25/00* | (2006.01) | |

(52) U.S. Cl.
CPC .......... *A61M 5/5086* (2013.01); *A61M 25/01* (2013.01); *A61M 25/0105* (2013.01); *A61M 5/158* (2013.01); *A61M 2025/0008* (2013.01); *A61M 2025/0175* (2013.01); *A61M 2210/122* (2013.01)

(58) Field of Classification Search
CPC ...... A61M 2025/0175; A61M 25/0108; A61M 2210/122–2210/127; A61M 25/065; A61M 2025/0039; A61M 2025/0004; A61M 25/0606; A61M 25/01; A61B 2017/00991; A61B 17/2909; A61B 17/3431; A61B 17/3417; A61B 2017/3433
See application file for complete search history.

(56) References Cited

U.S. PATENT DOCUMENTS

| | | | | |
|---|---|---|---|---|
| 4,869,717 A | * | 9/1989 | Adair ................ | A61B 17/3496 604/164.06 |
| 4,968,306 A | * | 11/1990 | Huss .................. | A61M 25/007 604/264 |
| 5,104,381 A | * | 4/1992 | Gresl ................ | A61B 1/00135 604/158 |
| 5,330,496 A | | 7/1994 | Alferness | |
| 8,311,648 B1 | | 11/2012 | Chitre et al. | |
| 2002/0055716 A1 | * | 5/2002 | Nakagami ......... | A61M 25/0631 604/164.12 |
| 2004/0097819 A1 | * | 5/2004 | Duarte ................ | A61B 5/0422 600/509 |
| 2007/0270741 A1 | * | 11/2007 | Hassett ............. | A61M 25/0084 604/96.01 |
| 2008/0051821 A1 | * | 2/2008 | Gephart ............ | A61B 17/0218 606/191 |
| 2009/0209912 A1 | * | 8/2009 | Keyser ............. | A61M 25/0606 604/164.1 |

(Continued)

FOREIGN PATENT DOCUMENTS

| | | |
|---|---|---|
| CN | 201551709 U | 8/2010 |
| CN | 202859885 U | 4/2013 |
| WO | 9315791 | 8/1993 |

*Primary Examiner* — Kevin C Sirmons
*Assistant Examiner* — Tiffany Legette-Thompson
(74) *Attorney, Agent, or Firm* — David H. Chervitz

(57) ABSTRACT

A pericardial access device includes a first tube, a second tube coupled to the first tube, and a biasing mechanism coupled to the second tube. The pericardial access device is moveable between an expanded configuration and a contracted configuration. The biasing mechanism biases the pericardial access device towards the expanded configuration, and the pericardial access device moves towards the contracted configuration when a force is applied to the second tube.

13 Claims, 2 Drawing Sheets

(56) References Cited

U.S. PATENT DOCUMENTS

| | | | |
|---|---|---|---|
| 2011/0112507 A1* | 5/2011 | Linderman | A61B 17/8819 604/506 |
| 2011/0282195 A1* | 11/2011 | Solar | A61M 25/0026 600/431 |
| 2012/0238968 A1 | 9/2012 | Toy et al. | |
| 2013/0211330 A1* | 8/2013 | Pedersen | A61M 5/2033 604/111 |
| 2013/0274782 A1 | 10/2013 | Morgan | |

* cited by examiner

PERICARDIAL ACCESS DEVICE AND ITS METHODS OF USE

BACKGROUND

The subject matter described herein relates generally to medical devices and, more particularly, to a pericardial access device configured to access a pericardial cavity or space.

Medical devices are known to access a pericardial space for diagnostic and/or therapeutic purposes. The pericardial space is at least partially defined by a pericardium. The pericardium is a double-walled sac that substantially covers the heart. Due to the proximity of the pericardial space to the heart, percutaneously accessing the pericardial space through the pericardium may increase a risk of heart perforation, which may endanger and/or traumatize a patient.

BRIEF SUMMARY

In one aspect, a method is provided for using a pericardial access device to access a pericardial space. The access device includes a first tube, a second tube coupled to the first tube such that the pericardial access device is moveable between an expanded configuration and a contracted configuration, and a biasing mechanism that biases the pericardial access device towards the expanded configuration. The method includes positioning a distal end of the second tube adjacent a surface, advancing the pericardial access device to contact the surface, such that a force is applied to the second tube and the pericardial access device moves towards the contracted configuration, and advancing the pericardial access device towards the pericardial space while the pericardial access device is in the contracted configuration until at least the distal end of the second tube penetrates the surface.

In another aspect, a pericardial access device is provided for accessing a pericardial space. The pericardial access device includes a first tube, a second tube coupled to the first tube, and a biasing mechanism that biases the pericardial access device towards the expanded configuration. The pericardial access device is moveable between an expanded configuration and a contracted configuration. The pericardial access device moves towards the contracted configuration when a force is applied to the second tube.

The features, functions, and advantages described herein may be achieved independently in various embodiments of the present disclosure or may be combined in yet other embodiments, further details of which may be seen with reference to the following description and drawings.

DETAILED DESCRIPTION

The methods and apparatus described herein relate to medical devices and, more particularly, to a pericardial access device configured to provide controlled access to a pericardial space. In some embodiments, the pericardial access device includes a first tube, a second tube coupled to the first tube such that the medical device is moveable between an expanded configuration and a contracted configuration, and a biasing mechanism that biases the pericardial access device towards the expanded configuration, and moves towards the contracted configuration when a force is applied to the second tube. The pericardial access device described herein provides access to the pericardial space in a controlled manner, such that a risk of heart perforation may be reduced.

As used herein, an element or step recited in the singular and preceded with the word "a" or "an" should be understood as not excluding plural said elements or steps, unless such exclusion is explicitly stated. Further, references to an "embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Figure 1:
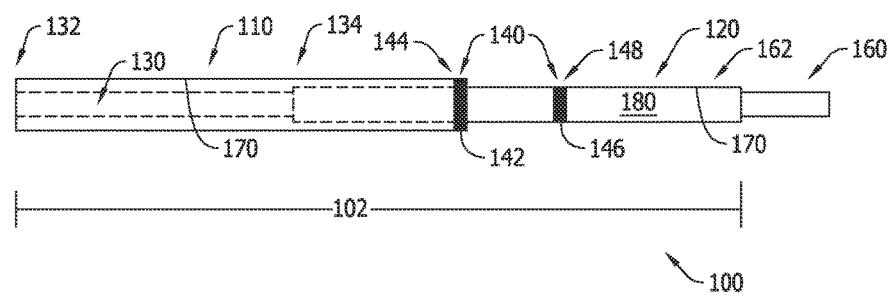
FIG. 1 is a schematic illustration of an exemplary pericardial access device in an expanded configuration.
Figure 2:
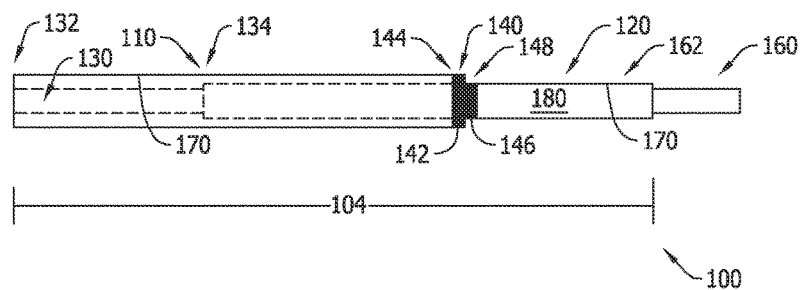
FIG. 2 is a schematic illustration of the pericardial access device shown in FIG. 1 in a contracted configuration.

FIGS. 1 and 2 are schematic illustrations of an exemplary pericardial access device 100. Pericardial access device 100 has an elongated body that is moveable between an expanded configuration (shown in FIG. 1) and a contracted configuration (shown in FIG. 2). For example, in the exemplary embodiment, pericardial access device 100 has a first length 102 when pericardial access device 100 is in the expanded configuration, and has a second length 104 less than first length 102 when pericardial access device 100 is in the contracted configuration.

Pericardial access device 100 includes a first tube 110, and a second tube 120 coupled to first tube 110. In the exemplary embodiment, first tube 110 is an outer sheath, and second tube 120 is an inner sheath at least partially positioned within the outer sheath, such that first tube 110 and second tube 120 are arranged in a telescopic configuration. Alternatively, first tube 110 and/or second tube 120 may be arranged in any configuration that enables pericardial access device 100 to function as described herein.

Pericardial access device 100 includes a biasing mechanism 130 positioned between at least a portion of first tube 110 and at least a portion of second tube 120. In the exemplary embodiment, biasing mechanism 130 is coupled to first tube 110 and/or second tube 120. In the exemplary embodiment, biasing mechanism 130 is in a relaxed state when pericardial access device 100 is in the expanded configuration, and is in a tensed state when pericardial access device 100 is in the contracted configuration. In the exemplary embodiment, pericardial access device 100 is biased towards the expanded configuration and moves away from the expanded configuration (i.e., increases or decreases in length relative to first length 102) when a force is applied to pericardial access device 100 or, more particularly, biasing mechanism 130. A movement of first tube 110 relative to second tube 120 "charges" biasing mechanism 130 (e.g., moves biasing mechanism 130 away from the relaxed state and/or increases a spring force associated with biasing mechanism 130).

In the exemplary embodiment, biasing mechanism 130 is a spring positioned within first tube 110 and between a proximal end 132 of first tube 110 and a proximal end 134 of second tube 120. In the exemplary embodiment, biasing mechanism 130 is coupled to proximal ends 132 and/or 134, such that biasing mechanism 130 spans the distance between a distal surface of first tube proximal end 132 and a proximal surface of second tube proximal end 134. In the exemplary embodiment, biasing mechanism 130 expands as pericardial access device 100 is moved towards the expanded configuration and/or as the distance between first and second tubes 110 and 120 increases, and contracts as pericardial access device 100 is moved towards the contracted configuration and/or as the distance between first and second tubes 110 and 120 decreases. For example, biasing mechanism 130 may be a cylinder, hydraulics, oil, and/or any other shock-absorber mechanism. Alternatively, biasing mechanism 130 may be any device and/or be coupled to any portion of pericardial access device 100 that enables pericardial access device 100 to function as described herein.

Pericardial access device 100 includes an indicating mechanism 140 configured to indicate whether pericardial access device 100 is in the contracted configuration and/or the expanded configuration. For example, in at least some embodiments, indicating mechanism 140 enables a user to visually, audibly, and/or tactilely monitor a relative positioning of first tube 110 and second tube 120 as pericardial access device 100 moves between the expanded configuration and the contracted configuration. For example, in one embodiment, indicating mechanism 140 includes a light source, a sound source, and/or a vibration source. In such an embodiment, indicating mechanism 140 may generate an alert when an electric circuit (as a switch) is closed or open.

In the exemplary embodiment, indicating mechanism 140 includes a first marker 142 extending about first tube 110 adjacent a distal end 144 of first tube 110, and a second marker 146 extending about second tube 120 at a location 148 remote from distal end 144 of first tube 110 when pericardial access device 100 is in the expanded configuration, and adjacent distal end 144 of first tube 110 when pericardial access device 100 is in the contracted configuration. Alternatively, indicating mechanism 140 may be any device and/or be coupled to any portion of pericardial access device 100 that enables pericardial access device 100 to function as described herein.

In the exemplary embodiment, pericardial access device 100 includes a sensor (not shown) configured to detect a movement of first tube 110 and/or second tube 120 and/or a pressure at a distal end of pericardial access device 100. In the exemplary embodiment, the sensor is configured to transmit a signal associated with the detection to indicating mechanism 140. For example, in at least some embodiments, the sensor is an electric or piezoelectric sensor configured to detect a position and/or movement of first tube 110 and/or second tube 120. Additionally or alternatively, the sensor is a pressure sensor configured to detect a pressure and/or a pressure change at the distal end of pericardial access device 100. In at least some embodiments, pericardial access device 100 includes a single tube (i.e., a tube that is not arranged in a telescopic configuration with another tube) that includes and/or is coupled to a sensor at a distal tip of the single tube.

In the exemplary embodiment, indicating mechanism 140 generates a visual, audial, and/or tactile indication and/or alert associated with the detection based on the signal received from the sensor. Alternatively, the sensor may be any device and/or be coupled to any portion of pericardial access device 100 that enables pericardial access device 100 to function as described herein. In at least some embodiments, a position and/or movement of first tube 110 and/or second tube 120 may be automatically controlled based on the signal received from the sensor.

In at least some embodiments, pericardial access device 100 includes and/or is coupled to a computing system including a memory device (not shown) and a processor (not shown) coupled to the memory device. In such embodiments, the computing system enables indicating mechanism 140 and/or the sensor to function and/or communicate with each other. In such embodiments, the computing system is configurable to perform one or more operations described herein by programming the memory device and/or processor.

As used herein, the term "processor" is not limited to integrated circuits referred to in the computing arts, but rather broadly refers to a controller, a microcontroller, a microcomputer, a programmable logic controller (PLC), an application specific integrated circuit, and other programmable circuits. Moreover, the term "memory device" refers to a device that enables information such as executable instructions and/or other data to be selectively stored and retrieved.

In the exemplary embodiment, pericardial access device 100 includes a puncturing mechanism 160 configured to puncture a surface (e.g., a skin surface or a pericardium surface) and/or enable pericardial access device 100 to traverse through tissue. In the exemplary embodiment, puncturing mechanism 160 is a needle coupled to a distal end of second tube 120. In at least some embodiments, the needle has a beveled tip and is hollow, such that a fluid and/or object may be channeled therethrough. Alternatively, a distal end 162 of second tube 120 is configured to puncture the surface. In one embodiment, puncturing mechanism 160 is sized and/or configured to enable a distal end of puncturing mechanism 160 to puncture a surface (e.g., a pericardium surface) while first tube 110 and/or second tube 120 are not subcutaneous (i.e., first tube 110 and second tube 120 stay outside of the body). Puncturing mechanism 160 may be any device, be coupled to any portion of pericardial access device 100, and/or be a part of any portion of pericardial access device 100 that enables pericardial access device 100 to function as described herein.

In the exemplary embodiment, first tube 110 and/or second tube 120 has an inner surface 170 that defines a lumen 180 configured to channel a fluid and/or an object therethrough. For example, in one embodiment, a guidewire is positioned within lumen 180 to facilitate guiding pericardial access device 100. Additionally or alternatively, lumen 180 channels blood when second tube 120 and/or puncturing mechanism 160 punctures a heart, and the blood is channeled into pericardial access device 100 via a distal opening defined at a distal end of second tube 120 and/or puncturing mechanism 160. In at least some embodiments, first tube 110 and/or second tube 120 is fabricated from a transparent material, such that the fluid and/or object being channeled through lumen 180 is visible to the naked eye through a sidewall of first tube 110 and/or second tube 120.

In at least some embodiments, pericardial access device 100 includes a valve (not shown) that is configured to selectively provide access to lumen 180. For example, in at least some embodiments, the valve is selectively moveable between an open configuration that provides access to lumen 180 and a closed configuration that restricts access to lumen 180.

In at least some embodiments, pericardial access device 100 includes a plunging mechanism (not shown) that is at least partially positioned and moveable within lumen 180 to facilitate channeling the fluid and/or object through lumen 180. For example, in one embodiment, a fluid and/or object is channeled through lumen 180 to facilitate radiologically and/or ultrasonically confirming a position of a distal end of second tube 120 and/or puncturing mechanism 160. Additionally or alternatively, the distal tip of second tube 120 and/or puncturing mechanism 160 is radio opaque and/or detectable by ultrasound. Alternatively, lumen 180 may interface and/or interact with any device and/or mechanism that enables pericardial access device 100 to function as described herein.

Figure 3:
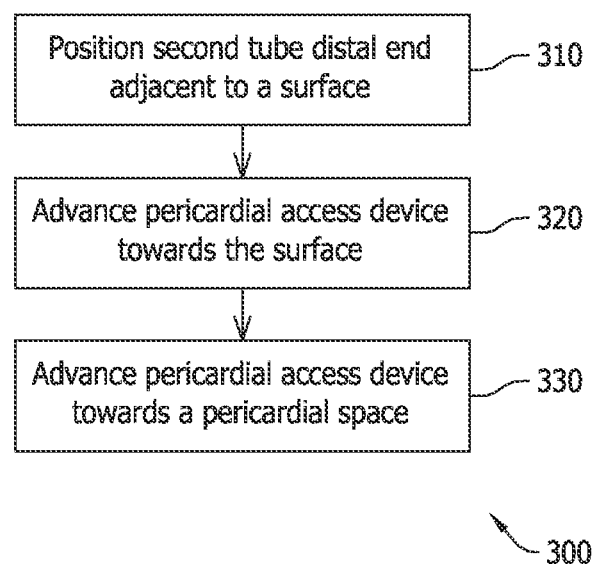
FIG. 3 is a flow chart illustrating an exemplary method of using the pericardial access device shown in FIG. 1.

FIG. 3 is a flow chart illustrating an exemplary method 300 of using pericardial access device 100 to access a pericardial space. During operation, distal end 162 of second tube 120 is positioned 310 adjacent a surface (e.g., a skin surface or a pericardium surface). In some embodiments, a user holds first tube 110 to position second tube 120 adjacent the surface.

Pericardial access device 100 or, more specifically, first tube 110 is advanced 320 towards the surface (e.g., an operator and/or an apparatus pushes first tube 110 towards the surface to increase a force associated with pericardial access device 100), such that a force is applied to distal end 162 of second tube 120.

In the exemplary embodiment, when biasing mechanism 130 is not fully charged (i.e., biasing mechanism 130 is not in the contracted configuration) and the force applied to distal end 162 of second tube 120 is less than or equal to a predetermined threshold (i.e., a threshold associated with the surface), an increase in force associated with an advancement of first tube 110 is at least partially absorbed by biasing mechanism 130 and, thus, the advancement of first tube 110 moves pericardial access device 100 towards the contracted configuration. In at least some embodiments, advancement of first tube 110 moves first tube 110 relative to second tube 120 while second tube 120 remains substantially stationary relative to the surface. In at least some embodiments, a convergence of markers 142 and 146 and/or an increase in resistance indicates that pericardial access device 100 is approaching the contracted configuration.

In some embodiments, second tube 120 does not slide and/or move within first tube 110 when pericardial access device 100 is in the contracted configuration. In at least some embodiments, a proximal positioning of first marker 142 and second marker 146 (see FIG. 2) indicates that pericardial access device 100 is in the contracted configuration. When biasing mechanism 130 is fully charged (i.e., biasing mechanism 130 is in the contracted configuration) and the force applied to distal end 162 of second tube 120 is less than or equal to the predetermined threshold, an increase in force associated with an advancement of first tube 110 cannot be absorbed by biasing mechanism 130 and, thus, the advancement of first tube 110 directly increases the force applied to distal end 162 of second tube 120.

When the force applied to distal end 162 of second tube 120 exceeds or is greater than the predetermined threshold, further advancement of first tube 110 moves second tube 120 relative to the surface (e.g., forces distal end 162 of second tube 120 to puncture the surface, e.g., the skin surface, and/or traverse the subcutaneous and/or muscle layer). In at least some embodiments, puncturing mechanism 160 facilitates puncturing the skin surface and/or traversing the subcutaneous and/or muscle layer. When second tube 120 and/or puncturing mechanism 160 punctures the surface, the force applied to distal end 162 of second tube 120 decreases, and pericardial access device 100 moves towards the expanded configuration.

Pericardial access device 100 is advanced 330 towards a pericardial space while pericardial access device 100 is in the contracted configuration until at least distal end 162 of second tube 120 penetrates a surface (e.g., a pericardium surface). In some embodiments, when distal end 162 of second tube 120 clears the surface, pericardial access device 100 returns and/or moves towards the expanded configuration. In at least some embodiments, a divergence of markers 142 and 146 and/or a decrease in resistance indicates that pericardial access device 100 is returning to the expanded configuration.

Additionally or alternatively, in at least some embodiments, indicating mechanism 140 indicates that distal end 144 of first tube 110 and/or distal end 162 of second tube 120 is in the pericardial space. In some embodiments, fluid and/or an object is injected to the pericardial space through lumen 180 to facilitate radiologically and/or ultrasonically confirming a position of first tube distal end 144 and/or second tube distal end 162.

The embodiments described herein relate generally to medical devices and, more particularly, to methods and systems for providing controlled access to a pericardial space. The embodiments described herein enable a user to percutaneously access a pericardial space in a controlled manner. For example, the embodiments described herein enable a user to monitor a relative positioning of a first tube and a second tube as a pressure or force is applied to the second tube.

Exemplary embodiments of methods and systems for providing controlled access to a pericardial space are described above in detail. The methods and systems are not limited to the specific embodiments described herein, but rather, components of systems and/or steps of the method may be utilized independently and separately from other components and/or steps described herein. Each method step and each component may also be used in combination with other method steps and/or components. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A pericardial access device for accessing a body and a pericardial space between a pericardium surface and a heart, the pericardial access device comprising: a first tube having an inner surface that defines a lumen, an outer surface, a proximal end and a distal end, with the distal end of the first tube having a first diameter: a first marker extending about the first tube adjacent the distal end of the first tube; a second tube having an inner surface that defines a lumen formed therein, an outer surface, a proximal end and a distal end, with the distal end of the second tube having a second diameter with the second diameter being less than the first diameter, the proximal end of the second tube for fitting within the first tube and the distal end of the second tube extending out from the first tube: a second marker extending about the second tube and positioned at a location remote from the distal end of the first tube; wherein the lumen of the first tube and the lumen of the second tube form a continuous lumen, a plunging mechanism partially positioned and moveable within the continuous lumen to facilitate channeling of a fluid or object through the lumen, a puncturing mechanism coupled to the distal end of the second tube, the puncturing mechanism having a third diameter, with the third diameter being less than the second diameter: and a biasing mechanism positioned within the first tube and between the proximal end of the first tube and the proximal end of the second tube and coupled to the proximal end of the first tube and coupled to the proximal end of the second tube, the biasing mechanism for biasing the second tube relative to the first tube in an expanded configuration and the second tube capable of moving relative to the first tube to a contracted configuration when the distal end of the second tube encounters a force applied thereto, the second marker capable of moving relative to the first marker to be adjacent to the first marker to indicate that the device is in the contracted configuration when the second tube moves relative to the first tube when the distal end of the second tube encounters a force applied thereto and the second marker capable of moving relative to the first marker to not being adjacent to the first marker to indicate that the device is in the expanded configuration with the device being initially in the expanded configuration then in the contracted configuration when the device is accessing the body and the distal end of the second tube encounters a force applied thereto, and then in the expanded configuration when the device has entered into the pericardial space in which the distal end of the second tube does not encounter a force applied thereto, and the first marker and the second marker staying outside of the body when the puncturing mechanism punctures a surface for the first marker and the second marker to be visible.

2. A pericardial access device in accordance with claim 1, wherein the biasing mechanism is a shock-absorber mechanism.

3. A pericardial access device in accordance with claim 1 wherein the puncturing mechanism is a needle.

4. A pericardial access device in accordance with claim 1 wherein the biasing mechanism is an oil shock absorber mechanism.

5. A pericardial access device in accordance with claim 1 wherein the biasing mechanism is a hydraulic shock absorber-mechanism.

6. A pericardial access device in accordance with claim 1 wherein the lumen provides a channel for positioning a guidewire within the lumen.

7. A pericardial access device in accordance with claim 1 wherein the puncturing mechanism extends out from the distal end of the second tube, the puncturing mechanism for puncturing through the body.

8. A pericardial access device in accordance with claim 1, wherein the lumen provides a channel for a fluid flow.

9. A pericardial access device in accordance with claim 1 wherein the first tube is fabricated from transparent material.

10. A pericardial access device in accordance with claim 1, wherein the biasing mechanism is a spring.

11. A pericardial access device in accordance with claim 1, wherein the first tube and the second tube are fabricated from transparent material.

12. A pericardial access device in accordance with claim 1 wherein the puncturing mechanism comprises a needle extending out from the distal end of the second tube, the needle for puncturing through the pericardium surface when the distal end of the second tube encounters the pericardium surface.

13. A pericardial access device in accordance with claim 12 wherein the needle comprises a beveled tip and is hollow to allow for fluid flow therein.

* * * * *